United States Patent
Chiesi et al.

(10) Patent No.: US 6,667,056 B2
(45) Date of Patent: Dec. 23, 2003

(54) PHARMACEUTICAL COMPOSITIONS CONTAINING AN EFFERVESCENT ACID-BASE COUPLE

(75) Inventors: Paolo Chiesi, Parma (IT); Paolo Ventura, Parma (IT); Rosa Mezzadri, Parma (IT); Gaetano Brambilla, Parma (IT); Daniela Acerbi, Parma (IT)

(73) Assignee: Chiesi Farmaceutici S.p.A., Parma (IT)

(*) Notice: Subject to any disclaimer, the term of this patent is extended or adjusted under 35 U.S.C. 154(b) by 0 days.

(21) Appl. No.: 09/932,097

(22) Filed: Aug. 20, 2001

(65) Prior Publication Data

US 2002/0051752 A1 May 2, 2002

Related U.S. Application Data

(63) Continuation-in-part of application No. 09/463,224, filed as application No. PCT/EP98/04517 on Jul. 23, 1998, now Pat. No. 6,284,272.

(30) Foreign Application Priority Data

Jul. 23, 1997 (IT) .................................... MI97A001746

(51) Int. Cl.$^7$ ................................................. A61K 9/46
(52) U.S. Cl. ........................ 424/466; 424/424; 514/282; 514/226.5; 514/284
(58) Field of Search .................................. 424/464, 466; 514/282, 226.5, 284

(56) References Cited

U.S. PATENT DOCUMENTS

| | | | | |
|---|---|---|---|---|
| 4,603,123 A | * | 7/1986 | Chiesi et al. | 514/58 |
| 5,055,306 A | * | 10/1991 | Barry et al. | 424/466 |
| 5,587,172 A | * | 12/1996 | Cherukuri et al. | 424/401 |
| 5,622,719 A | * | 4/1997 | Myers et al. | 424/439 |
| 5,762,951 A | * | 6/1998 | Maasz et al. | 424/439 |

FOREIGN PATENT DOCUMENTS

EP  0 396 335 A1  11/1990

* cited by examiner

Primary Examiner—Thurman K. Page
Assistant Examiner—Amy E Pulliam
(74) Attorney, Agent, or Firm—Oblon, Spivak, McClelland, Maier & Neustadt, P.C.

(57) ABSTRACT

A pharmaceutical formulation in the form of a fast dissolving tablet comprising an active ingredient, sodium glycine carbonate and an acid capable of reacting rapidly with sodium glycine carbonate to release carbon dioxide.

13 Claims, No Drawings

PHARMACEUTICAL COMPOSITIONS CONTAINING AN EFFERVESCENT ACID-BASE COUPLE

This application is a Continuation-in-part (CIP) of application Ser. No. 09/463,224 Filed on Mar. 21, 2000, now U.S. Pat. No. 6,284,272 which was originally filed as international Application Number PCT/EP98/04517 on Jul. 23, 1998.

BACKGROUND OF THE INVENTION

Field of the Invention

This invention relates to orally administered, solid, fast-soluble pharmaceutical compositions containing an effervescent acid-base couple, suitable for dissolving in water or an aqueous solution and for sucking.

The effervescent tablets occupy an important position among dosage forms, being the form of choice not only for adults but also for children. Many drugs, and in particular analgesics, vitamins and antibiotics were designed in this kind of formulations.

The effervescent tablets, when added to cold water, generate a gas which causes effervescence and produces a clear sparkling solution. The gas which gives the effervescence is always carbon dioxide which derives from the reaction between an acid and a base like carbonate or bicarbonate. The effervescent tablet consists of at least three components:

- the active ingredient;
- an acid;
- an alkali compound (basic ingredient) constituted by a carbonate or a bicarbonate.

The acid and the alkali are the essential components which provide the effervescence and the disintegration of the tablet when is contacted with water. As acidic component the citric acid both in the hydrated and anhydrous forms is more often used, but other edible acids like tartaric, fumaric, adipic, malic acid can be used as well. The carbonate, which represents the source of carbon dioxide which generates the effervescence, generally is a water-soluble alkaline carbonate. The choice of the carbonate is very important since, besides provoking the effervescence, it can influence the stability of the tablet. Sodium bicarbonate is one of the most used carbonate because it is very soluble and of low cost. Alternatively, modified sodium bicarbonate can be used, obtained by heating common sodium bicarbonate in order to convert the surface of its particles to sodium carbonate so increasing its stability.

Other physiologically acceptable alkaline or alkaline earth metal carbonates may be used, such as potassium or calcium (bi)carbonate, sodium carbonate, or sodium glycine carbonate.

Compositions of effervescent tablets may also include a lubricant which has to be necessarily selected from the totally water soluble compounds forming a clear solution. Examples of this kind of lubricants are sodium benzoate, sodium acetate, fumaric acid, polyethylenglycols (PEG) higher than 4000, alanine and glycine.

Conventional excipients such as diluents, ligands, bufferings, sweeteners, flavourings, colorings, solubilizers, disintegrants, wetting agents and other excipients of common use may be added to the formulation. Effervescent tablets are convenient, attractive, easy to use premeasured dosage forms. These advantages, however, are balanced by some technological problems, the two most important of which are hygroscopicity and lubrication.

The instability of effervescent tablets, their tendency to absorb moisture and lose reactivity are generally known. Due to this instability in the presence of water, conventional wet granulation and the subsequent granulate compression are very hardly applicable.

Sometimes the granulation has been carried out using very low amounts of water, for example through the fusion of the citric acid monohydrate, which upon heating releases part of the water of crystallisation which acts as the granulating fluid. Then the granulate has to be processed in conditions of severely controlled relative humidity, normally lower than 20%.

Alternatively, techniques of anhydrous granulation, in the absence of aqueous phases, have been applied using volatile organic solvents like ethanol. However such techniques require special manufacturing environments with strictly controlled relative humidity conditions (normally lower than 20%) and with explosion proof equipment.

Another technique, which is more time-consuming and more laborious, is represented by the separated wet granulation of acidic and alkali granules, which are subsequently mixed and compressed to give the final pharmaceutical composition.

The direct compression of the simple physical blend of the components of the formulation represented an attempt to obviate the above technological difficulties. However such an operation has been carried out in controlled thermo-hygrometric conditions, for example at temperatures lower than 20–25° C. and with relative humidity lower than 30%, using tabletting machines with tapered dies and punches faced with chromium alloys.

Because of the operating and stability problems, this type of manufacturing method cannot be easily applied to the preparation of effervescent tablets of particular active ingredients which cannot be wet granulated or which contain a residual percentage of water of crystallisation which is hardly eliminated. Typical examples of this kind of medicaments are drug cyclodextrin complexes, hydrated active ingredients and their salts, which may present stability problems in the presence of water. Similar problems are encountered when the composition contains excipients having hydration water or residual-hardly eliminable moisture. Typical examples of this kind of excipients are cyclodextrins.

The other important technological problem affecting the manufacture of effervescent tablets is lubrication, as the lubricant must not only have lipophilic properties for good lubrication, but also high water solubility, to give adequate disintegration and produce quickly a clear solution. Most substances used as lubricants, such as magnesium stearate, are effective, but are water insoluble. The resulting solution after disintegration is cloudy and often has a soapy taste. Ideally, non toxic lubricants with high water solubility and acceptable taste are required. Moreover, the effervescent base is inherently difficult to lubricate, partly due to the nature of the raw materials used and partly due to the rapid tablet disintegration usually required which limits the use of high percentage of lubricants.

BRIEF SUMMARY OF THE INVENTION

Now it has been found, and this is an object of the present invention, that effervescent tablets can be prepared through simple techniques which have direct-industrial application and which are based on the use of a particular effervescent blend of acids and sodium glycine carbonate, provided in a sufficient amount to rapidly disperse and assist dissolution of the components of the formulation.

In particular, according to a second aspect of the invention, it was found that the use of a blend of certain acids with sodium glycine carbonate allows to prepare effervescent tablets by direct compression in normal thermohygrometric conditions and with standard tabletting equipment.

It has been even more surprisingly found that this technology applies also to active ingredients and/or excipients which cannot be wet-granulated or which contain a residual percentage of hardly eliminable crystallisation water.

According to a further aspect of the invention, it was found that the use of certain acids/sodium glycine carbonate blend is particularly advantageous in the preparation of effervescent tablets which contain a cyclodextrin as the component of an inclusion complex or as an excipient, despite of the fact that cyclodextrins have hydration water and tend to absorb moisture very easily.

DESCRIPTION OF RELATED ART

The characteristics of excipients which can be used in the preparation of effervescent tablets, have been described in Aiache J M, Pharm Acta Helv 49 (5/6), 169–178, 1974 and in Boymond C, Labo-Pharma Probl Tech 25(271), 987–995, 1977.

Anyway, Faguet J P et al. in Labo-Pharma Probl Tech 26(274), 207–210, 1978, after evaluating the effects of moisture on the stability of acids, carbonates and bicarbonates, conclude that when sodium glycine carbonate, which is per se moisture—sensitive, is blended with an acid, specifically citric acid, the resulting carbonate is very moisture—unstable, much more than sodium glycine carbonate alone.

In some patents, sodium glycine carbonate is simply mentioned, among various different excipients, as a possible component of effervescent combinations which can be used in chewable tablets (EP 396335), in formulations which form a suspension when contacted with water (EP 528846), in compositions constituted by separated acidic and alkali granules which can also comprise a moisture scavenger (ZA 9307745), in oral, cold-water soluble formulations of JS-cyclodextrin complexes with non steroidal anti inflammatory drugs like ibuprofen, naproxen or ketoprofen (WO 9504528).

However, none of the above documents teaches the preparation of effervescent tablets using sodium-glycine carbonate as the basic component, nor suggests the possible advantages thereof.

The use of sodium glycine carbonate in effervescent formulations is described in patent applications and scientific literature regarding formulations containing hydrated amoxycillin (PCT WO 9115197), isosorbide-5-mononitrate (DE 4416769) and enzymes (FR 2305194). The acidic component in these formulations is constituted of citric, tartaric, malic or adipic acid and the manufacturing process foresees steps of slugging, milling slugs, blending and compressing or the use of anhydrous excipients or, also, an external lubrication of the machine is performed.

Amela J. et al in the paper "Drug Dev Ind Pharm 22(5), 407–16, 1996" make the analysis of various components which can be used in the preparation of effervescent tablets and they conclude that sodium glycine carbonate is one of the carbonates which do not have favourable compressing characteristics.

The formulations of the invention essentially comprise:
an active ingredient;
sodium glycine carbonate;
an acid capable to react rapidly with sodium glycine carbonate to release carbon dioxide.

One of the preferred acids is fumaric acid which may be present in the form of salt such as mono sodium or potassium fumarate. Certain kinds of formulation take advantage by the lubricant properties of fumaric acid allowing to limit the quantity of lubricant.

Another preferred acid is maleic acid eventually present as a salt.

The choice of the acid is made according to the characteristics of the active ingredient. In some cases mixtures of acids and/or salts are particularly suitable to modulate either the strength of the acid or the lubricant properties.

The use of fumaric acid in effervescent formulations is described in several documents which refer to various formulations, but never in combination with sodium glycine carbonate.

EP 443381, FR 2715849, WO 9300886, WO 9107174, WO 9104757 are examples of patent literature which mention fumaric acid among other acids which are commonly used in the effervescent pharmaceutical forms such as U.S. Pat. Nos. 4,153,678, 4,812,303 and 4,704,269, referred to formulations of particular active ingredients. In other documents (among which for example GB 1178294, Roscheisen G. and Schmidt P C Eur J. Pharm. Biopharm 41(5), 302–308, 1995), fumaric acid is considered as a lubricant.

Maleic acid has been also described as an acidic component of effervescent couples but never in combination with sodium glycine carbonate.

DETAILED DESCRIPTION OF THE INVENTION

In a particular embodiment of the invention the active ingredient of the formulation contains residual percentage of moisture or of crystallization water hardly eliminable. Examples of this kind of active ingredients are complexes of drugs such as the piroxicam-β-cyclodextrin complex, levodopa methyl ester and carbidopa hydrate.

The piroxicam-β-cyclodextrin complex has been described in EP 153998, wherein also an effervescent tablet formulation is exemplified. In this case citric acid-sodium glycine carbonate represented the effervescent blend. However, tablets corresponding to the formulation exemplified in EP 153998, have unfavourable characteristics like the opacity of the produced solution, high dimension and weight and low flowability of the pondered blend to be compressed. Moreover, the presence of saccharose as diluent, and of sweetening agents, compromises the stability of the same formulation, as it has been afterwards ascertained.

The formulation may comprise other excipients like:
a lubricant selected from PEG higher than 4000 and preferably PEG 6000 sodium benzoate, sodium and potassium fumarate, leucine, alanine;
a sweetening agent selected from aspartame, saccharin, cyclamate, sugars, preferably aspartame;
a diluent selected from lactose, mannitol, sorbitol or mixtures thereof and preferably spray-dried (SD) lactose and optionally aromatizing agents, ligands, preservatives or others.

As a diluent SD lactose is particularly preferred in that it facilitates the blend flowability so improving compressibility and machinability of the formulation.

The particular effervescent blend of the invention, together with the above-mentioned additives, allows highly soluble, stable and small-sized effervescent tablets to be prepared by direct compressing the component mixture which can be worked at the standard thermo-hygrometric conditions of normal pharmaceutical production facilities, using standard to compressing machines with normal punches and dies. Also the subsequent processing, storage and packaging of the tablets can be performed at normal temperature and moisture conditions.

The effervescent compositions of the invention solubilize on contact with water and produce a clear solution for oral administration. Solutions are favoured over suspensions for oral administration, since drugs in solution are more rapidly absorbed. Solutions are also often more acceptable to patients, in terms of palatability. Nevertheless in some cases the active ingredient does not dissolve and the composition does not result in a clear solution, but a suspension. For this kind of active ingredient the possibility to prepare a tablet by direct compression and obtain a rapid disintegration anyway represents a remarkable formulation improvement.

Other advantages of the composition are the low content of sodium ions, due to the employ of sodium glycine carbonate, with respect to other sodium carbonates and the less fizzy effervescence, more pleasant to the patient.

Moreover the composition of the invention, because of its small size, light effervescence and rapid disintegration, can also be prepared as fast dissolving or sucking in the mouth. In fact, as introduced in the mouth, when in contact with saliva, the tablet disintegrates and rapidly forms a solution or an aqueous dispersion easily swallowable.

The following examples further illustrate the invention.

EXAMPLE 1

Composition of an effervescent tablet having a piroxicam content of 20 mg.

| | |
|---|---|
| Piroxicam-β-cyclodextrin complex (1:2,5) | 191.2 mg |
| Sodium glycine carbonate | 260.0 mg |
| Fumaric acid | 180.0 mg |
| PEG 6000 | 20.0 mg |
| Lactose spray-dried (SD) | 208.8 mg |
| Lemon flavour | 25.0 mg |
| Aspartame | 15.0 mg |

Piroxicam-β-cyclodextrin, lactose SD, sodium glycine carbonate, lemon flavour, aspartame and PEG 6000 are sieved and pre-mixed. Fumaric acid is added and the components are mixed until an homogeneous blend is obtained. Then the blend is compressed in a standard rotary tabletting machine equipped with round chromium plated punches. The process is carried out at room temperature and with a relative humidity not higher than 55–60%. The dimensions of the produced tablets are about 13 mm diameter, 5 mm thickness and the weight is about 900 mg.

EXAMPLE 2

Active ingredient solution test

The analysis of the tablets prepared according to the example 1 was carried out in order to determine the percentage of the dissolved active ingredient at the end of the effervescence. The maximum dissolution time with effervescence is 1.5 min. The experimental conditions simulated the intake of the effervescent tablets by the patient.

The effervescent tablet was dissolved in three kinds of water. At the end of the effervescence (1.5 min) the amount of piroxicam-β-cyclodextrin was determined in the solution. The data obtained, which are reported in table 1, demonstrate that the active ingredient concentration in the solution is always higher than 70% of the nominal content per tablet.

TABLE 1

Dissolution of piroxicam-β-cyclodextrin in 50 ml water

| Kind of water | % active ingredient dissolved |
|---|---|
| demineralized water | 72.4 |
| drinking water | 85.6 |
| natural no-gassed water | 77.0 |

EXAMPLE 3

Dissolution rate of effervescent tablets containing the piroxicam-β-cyclodextrin complex in comparison with standard tablets. The dissolution rate of effervescent tablets prepared in Example 1 was compared with that of standard piroxicam-β-cyclodextrin tablets using USP Apparatus 2 (paddles) in distilled water at a temperature of 37° C.

| | Dissolution time (minutes) | Dissolved piroxicam (%) |
|---|---|---|
| 20 mg standard tablets | 5 | 65% |
| | 10 | 100% |
| 20 mg effervescent tablets | 5 | 100% |

EXAMPLE 4

The oral absorption profile of piroxicam released from effervescent tablets of piroxicam-β-cyclodextrin complex (B-CD) prepared according to the present invention was compared to that of piroxicam-βCD commercially available standard tablets. The test was carried out after single oral dose administration of the two formulations, equivalent to 20 mg piroxicam, in sixteen healthy volunteers according to a randomized two—way crossover design.

The results, reported in table 2, confirmed the behaviour of the two compositions in the dissolution test showing a more rapid absorption of the active ingredient after administration of the effervescent formulation of the invention. Compared to the standard formulation, the effervescent tablet gives remarkably higher plasma concentrations (Cp of 1.93 μg/ml vs 0.77 μg/ml, respectively) 15 min after the administration, as well as a higher drug exposure during the first hour after the administration, as it is shown by the AUC data (AUC=Area Under the Curve, i.e. the area under the plasma concentration vs time curve) collected after 1 hour.

TABLE 2

Main pharmacokinetic parameters (geometric means standard deviation), statistical comparison and standard 90% confidential intervals (90% CI).

| Pharmacokinetic parameters | Piroxicam-β-CD tablets (n = 16) | Piroxicam-β-CD effervescent tablets (n = 16) | 90% CI p* |
|---|---|---|---|
| Cp 15 min 389% (μg/mL) | 0.77 (0.310–1.90) | 1.93 (1.33–2.80) | 160%– 0.003 |

TABLE 2-continued

Main pharmacokinetic parameters (geometric means standard deviation), statistical comparison and standard 90% confidential intervals (90% CI).

| Pharmacokinetic parameters | Piroxicam-β-CD tablets (n = 16) | Piroxicam-β-CD effervescent tablets (n = 16) | 90% CI p* |
|---|---|---|---|
| Cp 30 min (µg/mL) | 2.01 (1.47–2.73) | 2.26 (1.64–3.10) | 100%–127% 0.106 |
| Cp 45 min (µg/mL) | 2.15 (1.76–2.62) | 2.22 (1.66–2.97) | 94%–114% 0.570 |
| Cp 1 h (µg/mL) | 2.08 (1.75–2.46) | 2.09 (1.58–2.77) | 93%–109% 0.845 |
| Cmax (µg/mL) | 2.23 (1.83–2.72) | 2.35 (1.74–3.16) | 96%–116% 0.330 |
| AUC 1 h (µg · h/mL) | 1.55 (1.19–2.01) | 1.88 (1.40–2.53) | 107%–138% 0.018 |

*Significance level calculated from the analysis of the variance (ANOVA)
Cmax = Maximum plasma Concentration

EXAMPLE 5

The stability of the effervescent blend and tablets prepared according to the example 1 was tested at 25° C. and at different relative humidity conditions.

Both the effervescent blend and tablets stored at a relative humidity of 11%, 33%, 52% and 75% showed an increase in weight at the beginning of the study, and afterwards a slight weight decrease (see tables 3 and 4).

This behavior is due to two correlated phenomena: the moisture absorption and subsequent loss of carbon dioxide.

The moisture absorption prevails during the first days with respect to the carbon dioxide release.

The loss of carbon dioxide however was so low that the effervescence characteristics of the tablets were not influenced.

TABLE 3

Blend % weight variation at room temperature (about 25° C.) at different relative humidity (R.H.) conditions.

| R.H. | 1 | 2 | 3 | 4 | 7 | 9 | 11 |
|---|---|---|---|---|---|---|---|
| 11% | 0.06 | 0.09 | 0.11 | 0.09 | 0.08 | 0.07 | 0.07 |
| 33% | 0.22 | 0.24 | 0.23 | 0.22 | 0.21 | 0.20 | 0.20 |
| 52% | 0.30 | 0.30 | 0.29 | 0.29 | 0:27 | 0.27 | 0.27 |
| 75% | 0.42 | 0.42 | 0.41 | 0.40 | 0.35 | 0.33 | 0.34 |

TABLE 4

Tablets % weight variation at room temperature (about 25° C.) at different relative humidity (R.H.) conditions.

| R.H. | 1 | 2 | 3 | 4 | 7 | 9 | 11 |
|---|---|---|---|---|---|---|---|
| 11% | 0.05 | 0.10 | 0.14 | 0.10 | 0.08 | 0.07 | 0.07 |
| 33% | 0.19 | 0.20 | 0.20 | 0.18 | 0.17 | 0.16 | 0.16 |
| 52% | 0.26 | 0.25 | 0.24 | 0.23 | 0.21 | 0.21 | 0.20 |
| 75% | 0.17 | 0.15 | 0.13 | 0.12 | 0.08 | 0.07 | 0.07 |

The effervescent blend and tablets according, to the present invention absorb a very low quantity of water (3.5% for the blend and 3.0% for the tablets) even in very unfavourable storage conditions, for example 11 days at 75% relative humidity.

In these particularly unfavourable conditions, the chemical, technological and effervescence characteristics of the tablets are not substantially modified, as it results from tables 5 and 6.

TABLE 5

Moisture per cent values and blend purity after 11 day storage at different relative humidity conditions

| Test | Initial value | 11% R.H. | 33% R.H. | 52% R.H. | 75% R.H. |
|---|---|---|---|---|---|
| 1) Moisture (%) | 2.4 | 3.6 | 4.1 | 4.5 | 5.9 |
| 2) Purity | <0.005 | <0.005 | <0.005 | <0.005 | <0.005 |

TABLE 6

Chemical and technological characteristics of the tablets after 11 day storage at different-relative humidity conditions

| Test | Initial value | 11% R.H. | 33% R.H. | 52% R.H. | 75% R.H. |
|---|---|---|---|---|---|
| Effervescence characteristics (disint. ≦ 5 min) | conforms | conforms | conforms | conforms | conforms |
| 1) Moisture (%) | 2.5 | 3.3 | 3.9 | 4.4 | 5.5 |
| 2) Purity | <0.005 | <0.005 | <0.005 | <0.005 | <0.005 |

1) The percentage of moisture absorption was determined by the Karl Fischer method 2) The purity was estimated determining the percentage of 2-aminopyridine which is the main degradation product of piroxicam.

EXAMPLES—FROM 6 TO 14

With analogous process as described in Example 1 the following tablet formulations have been prepared:

EXAMPLE 6

| | Ambroxol hydrochloride | |
|---|---|---|
| a) | Ambroxol hydrochloride | 30 mg |
| | Lactose SD | 800 mg |

-continued

| Ambroxol hydrochloride | |
|---|---|
| Sodium Glycine Carbonate | 400 mg |
| Fumaric Acid | 260 mg |
| PEG 6000 | 40 mg |
| Aspartame | 30 mg |

The mixture is compressed directly into tablets with a diameter of 17 mm and a thickness of 5.5 mm.

| b) | Ambroxol hydrochloride | 60 mg |
|---|---|---|
| | Lactose SD | 600 mg |
| | Sodium Glycine Carbonate | 400 mg |
| | Maleic Acid | 250 mg |
| | PEG 6000 | 40 mg |
| | Aspartame | 30 mg |

The mixture is compressed directly into tablets with a diameter of 17 mm and a thickness of 5.0 mm.

EXAMPLE 7

| Paracetamol | |
|---|---|
| Paracetamol (acetaminophen) | 500 mg |
| Sodium Glycine Carbonate | 260 mg |
| Fumaric Acid | 180 mg |
| PEG 6000 | 10 mg |

The mixture is compressed directly into tablets with a diameter of 13 mm and a thickness of 5.1 mm.

EXAMPLE 8

| Paracetamol/Domperidone Maleate combination | |
|---|---|
| Paracetamol (acetaminophen) | 500 mg |
| Domperidone maleate | 10 mg |
| Sodium Glycine Carbonate | 400 mg |
| Fumaric Acid | 300 mg |
| PEG 6000 | 10 mg |
| Aspartame | 20 mg |

The mixture is compressed directly into tablets with a diameter of 15 mm and a thickness of 5.7 mm.

EXAMPLE 9

| Nimesulide | | |
|---|---|---|
| a) | Nimesulide | 50 mg |
| | Lactose SD | 500 mg |
| | Sodium Glycine Carbonate | 800 mg |
| | Fumaric Acid | 180 mg |
| | PEG 6000 | 40 mg |

The mixture is compressed directly into tablets with a diameter of 17 mm and a thickness of 5.2 mm.

| b) | Nimesulide | 50 mg |
|---|---|---|
| | Betacyclodextrin | 300 mg |
| | Lactose SD | 50 mg |
| | Sodium Glycine Carbonate | 300 mg |
| | Fumaric Acid | 180 mg |
| | PEG 6000 | 20 mg |

The mixture is compressed directly into tablets with a diameter of 13 mm and a thickness of 4.98 mm.

EXAMPLE 10

| Ibuprofen | |
|---|---|
| Ibuprofen | 200 mg |
| Lactose SD | 610 mg |
| Sodium Glycine Carbonate | 600 mg |
| Fumaric Acid | 360 mg |
| PEG 6000 | 30 mg |

The mixture is compressed directly into tablets with a diameter of 20 mm and a thickness of 5.2 mm.

EXAMPLE 11

| Morniflumate | |
|---|---|
| Morniflumate | 175 mg |
| Lactose SD | 300 mg |
| Sodium Glycine Carbonate | 650 mg |
| Fumaric Acid | 800 mg |
| PEG 6000 | 50 mg |

The mixture is compressed directly into tablets with a diameter of 20 mm and a thickness of 5.0 mm.

EXAMPLE 12

| Levodopa methyl ester (LDME) | |
|---|---|
| LDME | 314 mg |
| Lactose SD | 146 mg |
| Sodium Glycine Carbonate | 260 mg |
| Fumaric Acid | 180 mg |

The mixture is compressed directly into tablets with a diameter of 13 mm and a thickness of 5.0 mm.

EXAMPLE 13

| Carbidopa monohydrate | |
|---|---|
| Carbidopa monohydrate | 27 mg |
| Lactose SD | 433 mg |
| Sodium Glycine Carbonate | 260 mg |
| Fumaric Acid | 180 mg |

The mixture is compressed directly into tablets with a diameter of 13 mm and a thickness of 5.0 mm.

EXAMPLE 14

| LDME/Carbidopa monohydrate combination | |
|---|---|
| LDME | 314 mg |
| Carbidopa monohydrate | 27 mg |
| Lactose SD | 539 mg |
| Sodium Glycine Carbonate | 520 mg |
| Fumaric Acid | 360 mg |
| PEG 6000 | 40 mg |

The mixture is compressed directly into tablets with a diameter of 17 mm and a thickness of 5.0 mm.

EXAMPLES 15, 16 AND 17

Dissolution rates of the formulations of the examples 6, 7 and 14 determined with the USP Apparatus 2 (paddles).

EXAMPLE 15

Ambroxol Hydrochloride

Conditions: medium=HCl 0.1 N; volume=750 ml;

speed=50 rpm (rounds per minute); temperature=37° C.

time: 5 min

% of dissolved drug: 98%

EXAMPLE 16

Paracetamol

Conditions: medium=distilled water; volume=900 ml; speed=50 rpm;

temperature=37° C.

Time: 5 min

% of dissolved drug: 90.9%

EXAMPLE 17

LDME/Carbidopa monohydrate combination

Conditions: medium=HCl 0.1 N; volume=750 ml; speed=50 rpm;

temperature=37° C.

Time: 5 min

% of dissolved Carbidopa: 94%

% of dissolved LDME: 99%

EXAMPLE 18

| (a) Apomorphine tablets (5 mg) | |
|---|---|
| Amormorphine hydrochoride | 5.00 mg |
| Mannitol (Pearlitol ® DC 200) | 135.50 mg |
| Fumaric acid | 20.00 mg |
| Sodium Glycine Carbonate | 6.90 mg |
| Crosspovidone (Kollidon ® CL) | 10.00 mg |
| Aspartame | 0.30 mg |
| Fresh-flavour | 0.30 mg |
| Magnesium Stearate | 2.00 mg |
| (b) Amorphine tablets (10 mg) | |
| Apomorphine hydrochloride | 10.00 mg |
| Mannitol (Peariltol ® DC 200) | 130.40 mg |
| Fumaric acid | 20.00 mg |
| Sodium Glycine Carbonate | 6.90 mg |
| Crosspovidone (Kollidon ® CL) | 10.00 mg |
| Aspartame | 0.30 mg |
| Aluminum lake (E110 20%) | 0.10 mg |
| Fresh-flavour | 0.30 mg |
| Magnesium Stearate | 2.00 mg |
| (c) Apomorphine tablets (20 mg) | |
| Apomorphine hydrochloride | 20.00 mg |
| Mannitol (Pearlitol ® DC 200) | 119.50 mg |
| Fumaric acid | 20.00 mg |
| Sodium Glycine Carbonate | 6.90 mg |
| Crospovidone (Kollidon ® CL) | 20.00 mg |
| Aspartame | 0.30 mg |
| Aluminum lake (E11 20%) | 0.50 mg |
| Fresh-flavour | 0.30 mg |
| Magnesium Stearate | 2.50 mg |

Each mixture is directly compressed into round flat tablets with a diameter 9 mm and a thickness of 2.4 mm.

This disintegration time of the tablets, performed according to European Pharmacopoeia 3rd Ed., "Disintegration test for effervescent tablets", is less than 1 min.

EXAMPLE 19

The oral absorption profile of levodopa and carbidopa released from effervescent tablets of LDME/carbidopa monohydrate combination prepared according to example 14 was compared to that of levodopa/carbidopa monohydrate commercially available standard tablets (Sinemet®).

The study was carried out after single oral dose administration of the two formulations in six healthy volunteers according to a cross-over design.

The results, reported in tables 7 and 8 show a more rapid absorption and an active ingredients higher exposure during the first hours after administration of the effervescent formulation in comparison to the standard commercial formulation.

In the table Cp=plasma Concentration; Cmax=maximum plasma Concentration; Tmax=Time to maximum concentration; AUC1h, AUC2h, AUCt=Area Under the Curve of plasma concentration vs time after 1 hour, 2 hours and total, respectively.

TABLE 7

Main pharmacokinetic parameters of Levodopa
(geometric mean ± standard deviation)
after oral administration, of effervescent tablets of
LDME/Carbidopa monohydrate combination of example 14 vs standard
commercial tablets of Levodopa/Carbidopa monohydrate combination
(Sinemet ®) in six healthy volounteers

| Levodopa pharmacokinetic parameters | Sinemet ® tablets | LDME/Carbidopa effervescent tablets |
|---|---|---|
| Cp 15 min (ng/mL) | 1292 ± 321 | 2787 ± 1338 |
| Cp 30 min (ng/mL) | 965 ± 304 | 1705 ± 989 |
| Cp 45 min (ng/mL) | 1158 ± 703 | 1339 ± 882 |
| Cp 1 h (ng/mL) | 999 ± 541 | 1023 ± 691 |
| Cmax (ng/mL) | 2218 ± 1289 | 3000 ± 1592 |
| Tmax (h) | 0.6 ± 0.3 | 0.3 ± 0.2 |

TABLE 7-continued

Main pharmacokinetic parameters of Levodopa
(geometric mean ± standard deviation)
after oral administration, of effervescent tablets of
LDME/Carbidopa monohydrate combination of example 14 vs standard
commercial tablets of Levodopa/Carbidopa monohydrate combination
(Sinemet ®) in six healthy volounteers

| Levodopa pharmacokinetic parameters | Sinemet ® tablets | LDME/Carbidopa effervescent tablets |
|---|---|---|
| AUC 1 h (ng · h/mL) | 986 ± 466 | 1683 ± 1074 |
| AUC t (ng · h/mL) | 5473 ± 4678 | 5123 ± 4485 |

TABLE 8

Main pharmacokinetic parameters of Carbidopa
(geometric mean ± standard deviation)
after oral administration, of effervescent tablets of
LDME/Carbidopa monohydrate combination of example 14 vs standard
commercial tablets of Levodopa/Carbidopa monohydrate combination
(Sinemet ®) in six healthy volounteers.

| Levodopa pharmacokinetic parameters | Sinemet ® tablets | LDME/Carbidopa effervescent tablets |
|---|---|---|
| Cp 30 min (ng/mL) | 52 ± 31 | 46 ± 33 |
| Cp 45 min (ng/mL) | 52 ± 32 | 63 ± 46 |
| Cp 1 h (ng/mL) | 59 ± 39 | 66 ± 45 |
| Cp 1.5 h (ng/mL) | 69 ± 47 | 72 ± 46 |
| Cp 2 h (ng/mL) | 49 ± 32 | 68 ± 42 |
| Cmax ng/mL) | 75 ± 51 | 88 ± 65 |
| Tmax (h) | 2.6 ± 1.7 | 1.5 ± 0.8 |
| AUC 2 h (ng · h/mL) | 44 ± 12 | 105 ± 72 |
| AUC t (ng · h/mL) | 230 ± 144 | 255 ± 168 |

This application is a Continuation-in-Part of U.S. application Ser. No. 09/463,224, filed Mar. 21, 2000. The full text of that application is incorporated herein by reference.

What is claimed:

1. A pharmaceutical composition in form of effervescent or fast-dissolving tablet of a water-soluble blend comprising an active ingredient and an effervescent couple, the couple comprising an acidic component and an alkaline component, wherein the active ingredient is selected from the group consisting of piroxicam-β-cyclodextrin complex, ambroxol hydrochloride, piroxicam combined with a cyclodextrin as an excipient, and apomorphine hydrochloride, the acidic component is selected from the group consisting of fumaric acid, maleic acid and their salts and the alkaline component is sodium glycine carbonate.

2. A pharmaceutical composition according to claim 1, further comprising at least one additional excipient selected from the group consisting of ligands, lubricants, sweeteners, solubilizers, colourings, flavourings, diluents, disintegrants, wetting agents and mixtures thereof.

3. A pharmaceutical composition in form of effervescent or fast-dissolving tablet of a water-soluble blend comprising an active ingredient and an effervescent couple, the couple comprising an acidic component and an alkaline component, wherein the active ingredient is selected from the group consisting of piroxicam-β-cyclodextrin complex, ambroxol hydrochloride and piroxicam combined with a cyclodextrin as an excipient, the acidic component is selected from the group consisting of fumaric acid, maleic acid and their salts and the alkaline component is sodium glycine carbonate.

4. A pharmaceutical composition according to claim 3, further comprising at least one additional excipient selected from the group consisting of ligands, lubricants, sweeteners, solubilizers, colourings, flavourings, diluents, disintegrants, wetting agents and mixtures thereof.

5. A pharmaceutical composition in form of effervescent or fast-dissolving tablet of a water-soluble blend comprising an active ingredient and an effervescent couple, the couple comprising an acidic component and an alkaline component, wherein the active ingredient is apomorphine hydrochloride, the acidic component is selected from the group consisting of fumaric acid, maleic acid and their salts and the alkaline component is sodium glycine carbonate.

6. A pharmaceutical composition according to claim 5, further comprising at least one additional excipient selected from the group consisting of ligands, lubricants, sweeteners, solubilizers, colourings, flavourings, diluents, disintegrants, wetting agents and mixtures thereof.

7. A pharmaceutical composition according to claim 3 comprising a water-soluble lubricant.

8. A pharmaceutical composition according to claim 1 further comprising a diluent, wherein the diluent is spray-dried lactose.

9. A pharmaceutical composition in form of effervescent or fast-dissolving tablet comprising an active ingredient and an effervescent couple, the couple comprising an acidic component and an alkaline component, wherein the active ingredient is apomorphine hydrochloride, the acidic component is fumaric acid, or its salts and the alkaline component is sodium glycine carbonate and further comprising mannitol, crosspovidone and magnesium stearate.

10. A pharmaceutical composition according to claim 1 wherein the pharmaceutical composition comprises cyclodextrin as the component of an inclusion complex or as an excipient.

11. A pharmaceutical composition according to claim 3, wherein the pharmaceutical composition comprises cyclodextrin as the component of an inclusion complex or an excipient.

12. A pharmaceutical composition according to claim 1, wherein the active ingredient is piroxicam-β-cyclodextrin.

13. A pharmaceutical composition according to claim 1 wherein the active ingredient is ambroxol hydrochloride.

* * * * *